United States Patent [19]

Haber et al.

[11] Patent Number: 4,909,794
[45] Date of Patent: Mar. 20, 1990

[54] COMBINATION RETRACTABLE NEEDLE CANNULA AND CANNULA LOCK FOR A MEDICATION CARPULE

[75] Inventors: Terry M. Haber; Clark B. Foster, both of El Toro, Calif.

[73] Assignee: Habley Medical Technology Corporation, Laguna Hills, Calif.

[21] Appl. No.: 211,366

[22] Filed: Jun. 24, 1988

[51] Int. Cl.⁴ ............................................. A61M 5/32
[52] U.S. Cl. ................................. 604/195; 604/232; 604/110
[58] Field of Search ............... 604/232, 195, 200, 201, 604/203, 240, 242, 243, 241, 110

[56] References Cited

U.S. PATENT DOCUMENTS

| | | | |
|---|---|---|---|
| 1,526,824 | 2/1925 | Bock | 604/241 |
| 2,855,927 | 10/1958 | Henderson | 604/243 |
| 3,367,331 | 2/1968 | Brookfield | 604/243 |
| 4,187,848 | 2/1980 | Taylor | 604/243 |
| 4,490,142 | 12/1984 | Silvern | 604/241 |
| 4,808,169 | 2/1989 | Haber et al. | 604/195 |

*Primary Examiner*—John D. Yasko
*Attorney, Agent, or Firm*—Morland C. Fischer

[57] ABSTRACT

A combination retractable needle cannula and cannula lock which is to be interfaced with a prefilled medication carpule at the interior of a hypodermic syringe. The cannula lock includes a clamp having a pair of oppositely disposed jaws which are normally separated from one another so that the needle cannula can be releasably retained therebetween. In the preinjection state, the clamp is axially spaced from the carpule, and the jaws of the clamp are rotated towards one another to retain the cannula in an axially extended position for administering an injection. In the post-injection state, after the contents of the carpule have been expulsed via the cannula, the clamp is engaged and displaced by the carpule, whereby the jaws of the clamp rotate away from one another to release the cannula. The cannula may then be retracted within and completely surrounded by the empty carpule so that the cannula can be safely discarded after use while avoiding an accidental needle stick and the spread of a contagious, and possibly life threatening, disease.

28 Claims, 3 Drawing Sheets

COMBINATION RETRACTABLE NEEDLE CANNULA AND CANNULA LOCK FOR A MEDICATION CARPULE

BACKGROUND OF THE INVENTION

1. FIELD OF THE INVENTION

This invention relates to a combination needle cannula and cannula lock which is to be interfaced with a prefilled medication carpule at the interior of a hypodermic syringe so that the cannula can either be locked at an axially extended position for administering an injection or released from the axially extended position and retracted within and completely surrounded by said carpule, whereby the cannula may be safely discarded after use while avoiding an accidental needle stick and the possible spread of disease.

2. PRIOR ART

In U.S. patent application No. 176,305 filed Mar. 31, 1988, which application has been or will be assigned to the assignee of the present invention, safety syringes are disclosed which have a prefilled medication carpule, a double ended hypodermic needle cannula, and means by which the needle cannula may be relocated from an axially extended position, at which the contents of the medication carpule are injected into a targeted tissue area, to a retracted position, at which the cannula is retracted within and completely surrounded by the carpule. Moreover, a pair of movable jaws was also disclosed for either retaining the cannula in the axially extended position or releasing the cannula for retraction into the carpule.

The present invention is directed to another embodiment of a safety syringe and, more particularly, to an efficient and reliable locking means by which a double ended needle cannula may be either retained in an axially extended position for administering an injection or released from the axially extended position to be retracted within and surrounded by an empty medication carpule. However, rather than the generally one-piece locking arrangements which are characteristic of the safety syringes of the above-mentioned co-pending patent application, the presently disclosed locking means is characterized by multiple components, whereby to facilitate the manufacture and handling (i.e. during packaging) of the syringe. Nothing is known which is the same as or equivalent to the presently disclosed combination needle cannula and needle cannula locking means by which the position of a cannula relative to a medication carpule may be selectively and reliably controlled.

SUMMARY OF THE INVENTION

In general terms, a combination retractable needle cannula and needle cannula lock is disclosed to be interfaced with a prefilled medication carpule at the hollow cylinder of a hypodermic syringe. In the preinjection state, a first end of the needle cannula extends outwardly from the distal end of the syringe cylinder and the second end projects into the cylinder to communicate with the carpule so that an injection may be administered. Locking means are provided to releasably retain the cannula in the outwardly extending position relative to the cylinder during the administration of the injection. The locking means includes a clamp which is disposed axially from the carpule during packaging. The clamp has a pair of normally spaced jaws that are movable towards one another and into engagement with the cannula for locking the cannula therebetween. The locking means also includes a generally cylindrical sleeve which is sized to surround the clamp and thereby move the jaws thereof towards one another and into engagement with the cannula.

In the injection state, an axial force is applied to a piston stem, and an associated piston is moved axially and distally through the medication carpule to administer an injection. The second end of the needle cannula penetrates and is retained by the piston when the piston is advanced to the distal end of the carpule to expulse the fluid contents thereof via the cannula. The axial force being applied to the piston stem is transferred to the carpule by way of the piston, whereby to drive the carpule distally through the syringe cylinder and into contact with the needle retaining clamp. Accordingly, the clamp is displaced axially relative to the surrounding sleeve, such that the jaws of the clamp are now free to move away from one another and out of engagement with the cannula, whereby to permit the cannula to be removed from the jaws.

In the post-injection state, an axial pulling force is applied to the piston stem to relocate the piston proximally through the syringe cylinder. The needle cannula, which ahs been released by the clamp and retained by the piston, is, correspondingly, withdrawn from the clamp jaws and retracted into the empty medication carpule. Thus, the cannula is completely surrounded and shielded by the carpule, so that the cannula can be safely discarded after use while avoiding an accidental needle stick and the spread of a contagious, and possible life threatening, disease.

DESCRIPTION OF THE PREFERRED EMBODIMENT

Figure 1:
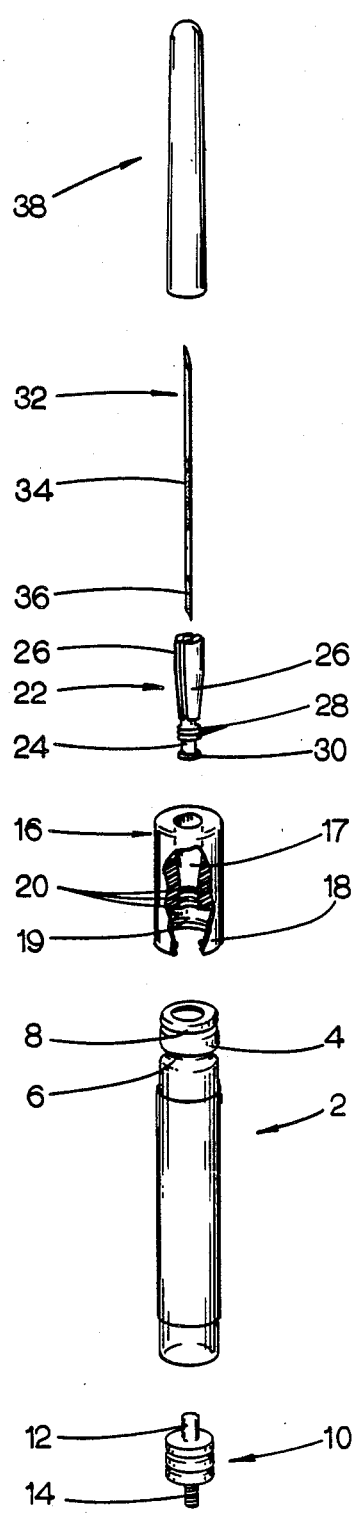
FIG. 1 is an exploded view of the combination retractable needle cannula and needle cannula lock which forms the present invention relative to a prefilled medication carpule.
Figure 6:
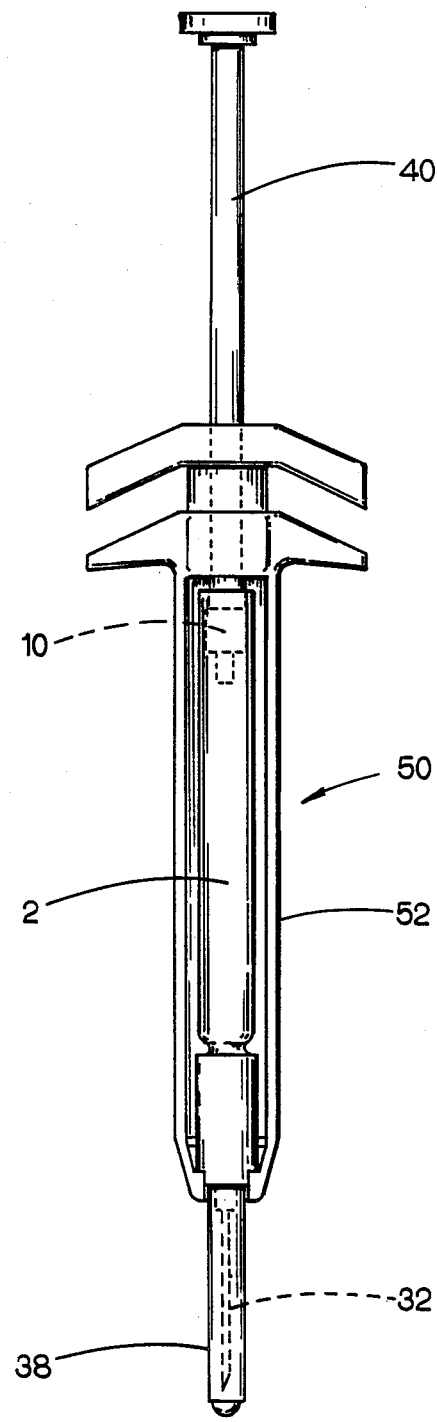
FIG. 6 is an example of a suitable syringe into which the combination needle cannula and cannula lock may be loaded and interfaced with a medication carpule to achieve the advantages of the present invention.

The combination retractable needle cannula and cannula lock which forms the present invention is best described while referring to the drawings, where FIG. 1 shows an exploded view of said combination in alignment with a disposable medication carpule, such as that designated by reference numeral 2. As illustrated in FIG. 6, the cannula, cannula lock, and medication carpule are adapted to be received within the hollow cylinder 52 of a commercially available syringe 50. Carpule 2 is of conventional design and includes a hollow, transparent body which is prefilled with a supply of fluid medication, or the like. Carpule 2 includes a head 4 and a cylindrical body which are coextensively joined together at a relatively narrow neck 6. A metallic end cap 8 covers a seal (designated 9 in FIG. 2) which extends across the carpule 2 to prevent contamination to and leakage of the fluid contents thereof.

A piston 10 is sized to be received in slidable axially and reciprocally through the interior of medication carpule 2. Piston 10 is formed from a relatively dense, resilient (e.g. rubber) material and includes an integral nub 12 projecting from one end thereof. As will soon be disclosed, the purpose of nub 12 is to engage and retain one end of the retractable needle cannula when the piston 10 is moved distally through the carpule 2 for expulsing the fluid contents of said carpule via the cannula. A screw-threaded rod 14 is connected to the piston 10 so as to project outwardly from the end of piston 10 which is opposite the nub 12. Screw-threaded 14 is to be mated to a correspondingly screw-threaded piston stem (designated 40 in FIG. 6) so as to complete a piston assembly for controlling the movement of piston 10 through the interior of carpule 2.

Figure 2:
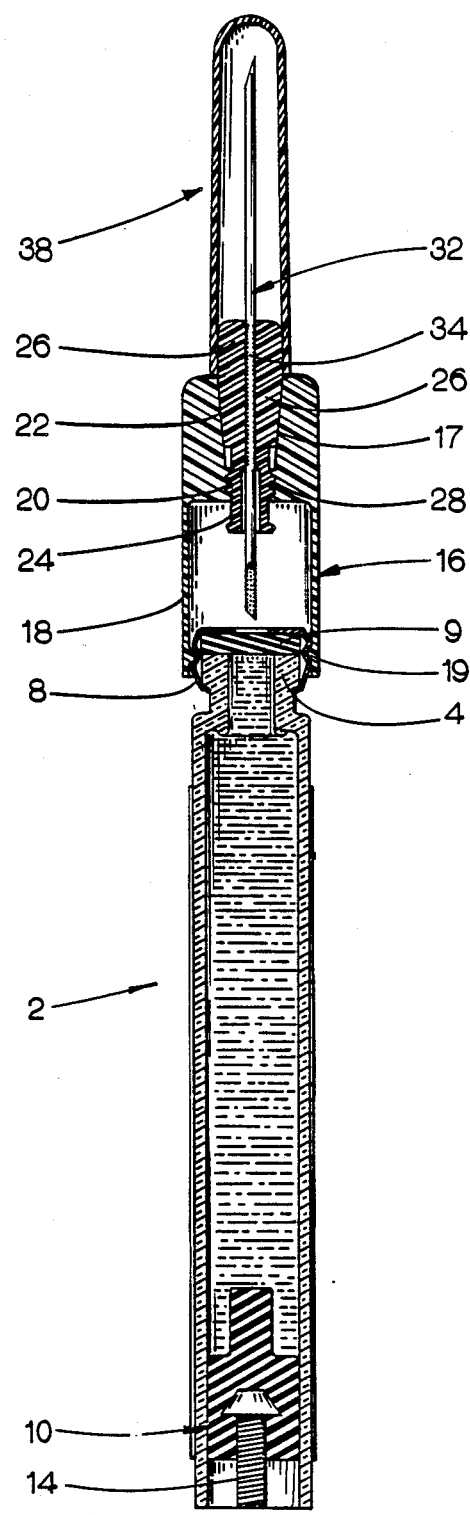
FIG. 2 shows the combination needle cannula and cannula lock of FIG. 1 aligned with the medication carpule in the packaged, preinjection state.

A generally hollow, cylindrical sleeve 16 is provided having a relatively narow, tapered bore 17 formed at the distal end thereof and a relatively wide body portion 18 formed at the proximal end which is sized to receive therewithin the head 4 of carpule 2. The sleeve 16 has a lower peripheral lip 19 extending around the interior of the proximal body portion 18 to enable sleeve 16 to be initially positioned with respect to carpule 2 during packaging (as best illustrated in FIG. 2). A series of alternating valleys and ridges or threads 20 extends around the periphery of the distal bore 17 of sleeve 16. As will be disclosed in greater detail hereinafter, the ridges 20 of sleeve 16 perform the important function of cooperating with complementary ridges of a soon to be described clamp or chuck 22 so as to either lock the needle cannula in an axially extended position for adminsitering an injection or release the needle cannula to be retracted within and completely surrounded by the medication carpule 2.

More particularly, the aforementioned clamp or chuck 22 includes a hollow, generally cylindrical base 24 and a pair of parallel aligned jaws 26. The jaws 26 are normally spaced from one another and adapted to rotate relative to the base portion 24 so as to releasably receive and reliably retain a needle cannula 32 in the space therebetween. The jaws 26 have a tapered configuration to match the taper of the distal bore 17 of sleeve 16. A series of alternating valleys and ridges or threads 28 extend around the exterior periphery of base 24 to be mated to the ridges 20 of sleeve 16. An annular lip 30 is formed around the bottom of base 24.

Cannula 32 is a conventional double ended needle cannula of the type commonly associated with certain hypodermic syringes. However, cannula 32 includes a high friction, raised or textured medial surface 34 and another high friction, textured surface 36 located adjacent the proximal end thereof. A removable needle sheath 38 is also provided to surround cannula 32 during storage and handling to preserve the sterility of the cannula and prevent an accidental needle stick prior to use.

FIG. 2 of the drawings shows the assembled relationship of the retractable needle cannula 32 and the cannula lock therefor relative to the medication carpule 2 during packaging and storage. More particularly, the relatively wide proximal body portion 18 of sleeve 16 receives and engages the head 4 of medication carpule 2, such that the lower peripheral lip 19 of said body portion 18 is snap-fit within a dimple that is typically formed in the end cap 8. The needle cannula 32 is moved into the space between the opposing jaws 26 of the clamp 22 and the combination needle cannula 32 and clamp 22 is then located within the distal bore 17 of sleeve 16 so as to secure cannula 32 in an axially extending position for administering an injection. That is, the receipt of the tapered jaws 26 of clamp 22 within the similarly tapered bore 17 of sleeve 16 forces the jaws to rotate towards one another and into frictional engagement with the cannula 32 at the medially disposed textured surface 34 thereof, to oppose any axial displacement of said cannula relative to clamp 22. Moreover, the ridges/threads 28 at the base 24 of clamp 22 are snapped or screwed into engagement with the complementary ridges/threads 20 at the distal bore 17 of sleeve 16 to oppose any axial displacement of the clamp 22 relative to sleeve 16.

In the preinjection or packaged state shown in FIG. 2, the needle cannula 32 is axially aligned with but spaced from the carpule 2. The piston 10 is located at the proximal end of carpule 2 so as to be connected (at the threaded rod 14 of piston 10) to a piston stem (designated 40 in FIG. 6) for completing a piston assembly so that the fluid contents of carpule 2 can be expulsed during the administration of an injection. The needle sheath 38 is snapped into engagement with clamp 22 so as to surround and protect the outwardly projecting distal end of cannula 32 prior to the administration of an injection.

Figure 3:
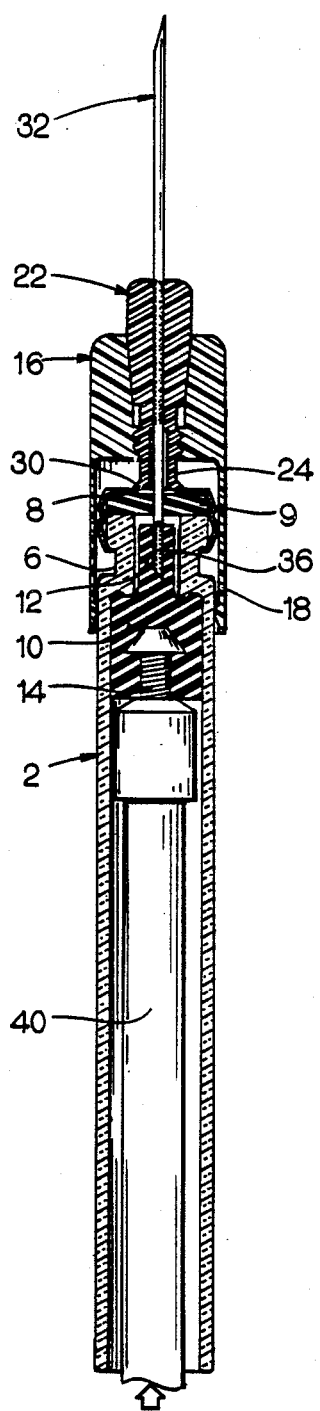
FIGS. 3 and 4 show the combination needle cannula and cannula lock interacting with the medication carpule during the injection state when the fluid contents of said carpule are expulsed via the cannula.
Figure 4:
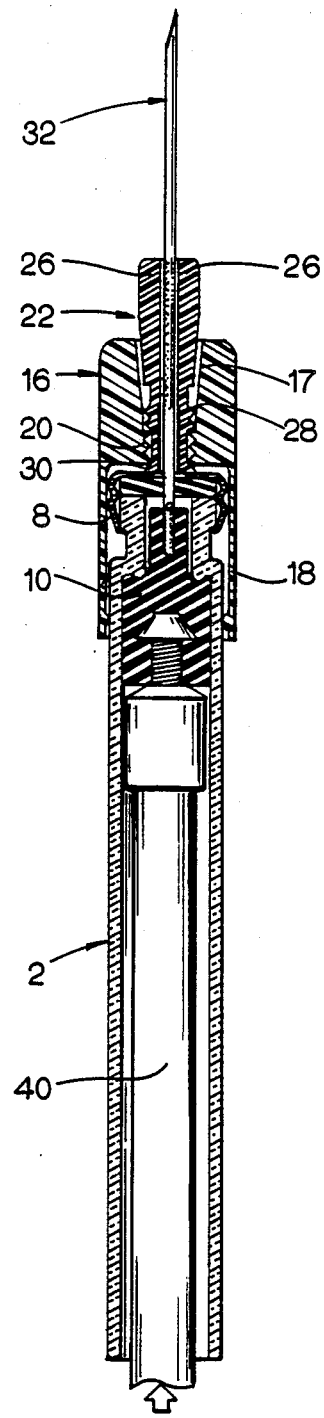
Figure 5:
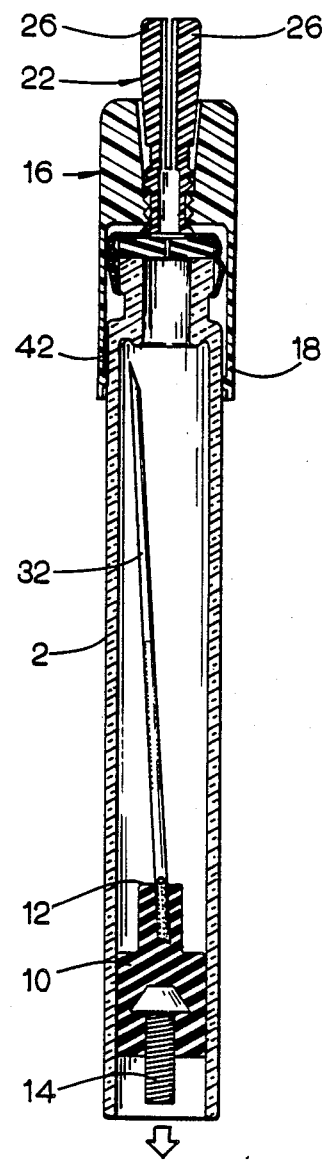
FIG. 5 shows the combination needle cannula and cannula lock during the post-injection state when the cannula is retracted within and surrounded by the carpule.

The operation of the combination needle cannula 32 and lock therefor during and after the administration of an injection is now described while referring to FIGS. 3–5 of the drawings. In the injection state of FIG. 3, the needle cannula 32, the cannula lock, and the medication carpule 2 of FIG. 2 are loaded into the cylinder of a suitable hypodermic syringe (designated 50 in FIG. 6) so that the distal end of the cannula extends outwardly from said cylinder. The carpule 2 is then advanced, by a health care worker, distally through the syringe cylinder and into the relatively wide proximal body portion 18 of sleeve 16. Accordingly, the inwardly extending proximal end of needle cannula 32 penetrates the end cap 8 and seal 9 of carpule 2 to communicate with the fluid contents of said carpule. Carpule 2 is continuously advanced through the proximal body portion 18 of sleeve 16 until the end cap 8 thereof is moved into contact with the annular lip 30 at the base 24 of clamp 22. The engagement of end cap 8 by lip 30 blocks the further distal displacement of the carpule 2 through the sleeve 16.

Next, the needle sheath (designated 38 in FIG. 6) is removed to expose the outwardly extending distal end of cannula 32. A screw-threaded piston stem 40 is connected to piston 10 at the screw-threaded rod 14 thereof. The cannula 32 is located at a targeted tissue area of the patient, and an axially and distally directed force is applied, by the health care worker, to piston stem 40. The distal force is transferred from piston stem 40 to the piston 10 to drive the piston through the medication carpule 2 and thereby expulse the fluid contents of said carpule via cannula 32.

At the conclusion of the injection, the piston 10 is located at the distal end of the medication carpule 2, such that the integral nub 12 of piston 10 is located within the neck 6 of said carpule, whereby the proximal end of cannula 32 penetrates the piston nub 12. The textured proximal surface 36 of cannula 32 enhances the retention of the cannula by the nub 12 and opposes the disconnection of the cannula from the nub.

After the injection has been administered and the needle cannula 32 received within and retained by the nub 12 of piston 10 at the distal end of carpule 2, the cannula 32 is released from the jaws 26 of clamp 22. That is to say, and referring to FIG. 4, the health care worker continues to apply an axially and distally directed force to the piston stem 40. The distally directed force is transferred from the piston stem to the empty medication carpule 2 via piston 10. More particularly, the piston 10 engages the distal end of carpule 2, so that any axially and distally directed force which is applied to said piston is also applied to the carpule. Accordingly, the carpule 2 is advanced distally through the interior of sleeve 16 until the end cap 8 of carpule 2 is located at the interface of the relatively wide body portion 18 with the relatively narrow distal bore 17.

Inasmuch as the clamp 22 is axially aligned with and engaged (i.e. at the annular lip 30 thereof) by the end cap 8 of carpule 2, the distal advancement of carpule 2 through sleeve 16 causes a corresponding distal advancement of clamp 22. That is, the axial force applied to clamp 22 (by way of piston stem 40, piston 10, and carpule 2) overcomes the interconnection of the ridges 28 of clamp 22 with the ridges 20 of sleeve 16. Hence, the clamp 22 is displaced axially relative to the sleeve 16 and, more particularly, distally relative to the distal bore 17 of said sleeve, whereby to permit the opposing jaws 26 of clamp 22 to rotate away from one another and out of engagement with the needle cannula 32. Therefore, the cannula 32 is now supported only by the piston 10 and is free to be removed from clamp 22.

FIG. 5 of the drawings illustrates the needle cannula 32 in the post-injection or retracted state, so that said cannula 32 is located within and completely surrounded by the empty medication carpule 2. More particularly, the health care worker applies an axial and proximal pulling force to the piston stem (designated 40 in FIG. 6) to relocate cannula 32 from the outwardly extended position, at which the injection was administered, to a relatively proximal position within carpule 2. The pulling force applied to the piston stem is transferred to the needle cannula 32 via the piston 10. Accordingly, the cannula 32 is withdrawn from the jaws 26 of clamp 22 and retracted within the carpule 2. By virtue of the foregoing, the cannula 32 is safely shielded by the carpule, whereby to avoid an accidental, and possibly life threatening, needle stick. Thereafter, the piston stem may be detached from the rod 14 of piston 10 and discarded. The carpule 2 may be popped out of the syringe cylinder and, likewise, discarded.

As an additional advantage of the present invention, the attachment of cannula 32 to the relatively dense, resilient material of the nub 12 of piston 10 will cause said cannula to be automatically canted when the cannula is retracted into the carpule 2. To this end, the carpule 2 may be formed with an optional, annular groove 42 that is positioned around the carpule so as to receive canted cannula 32 and thereby prevent the possible return of the cannula to the axially extended position (of FIG. 3) in the event that the piston stem (and the cannula connected thereto) is inadvertently moved axially and distally through the carpule 2.

FIG. 6 of the drawings illustrates a preferred example of a syringe 50 into which the assembly of FIG. 2 may be loaded in order to obtain the benefits of the presently disclosed invention. Syringe 50 includes a hollow cylinder 52 having an open side through which the medication carpule 2 is to be inserted and subsequently removed. Such a syringe 50 has particular application as a reusable dental syringe and is known commercially under the name CARPUJECT manufactured by Winthrop-Breon Corporation of New York. Reference may be made to copending U.S. patent application Ser. No. 181,204 filed Apr. 13, 1988 for a more detailed description of the operation of syring 50 and, more particularly, the manner by which the piston stem 40 is connected to piston 10 and the means by which the medication carpule 2 is moved distally through cylinder 52 and into fluid communication with the needle cannula 32. However, it is to be expressly understood that the reusable dental syringe 50 illustrated in FIG. 6 is for purposes of example only, and, therefore, other suitable reusable and disposable syringes are also applicable herein.

It will be apparent that while a preferred embodiment of the invention has been shown and described, various modifications and changes may be made without departing from the true spirit and scope of the invention. For example, although the clamp 22 has been described as moving axially and distally relative to the distal bore 17 of sleeve 16, it is within the scope of the claimed invention to otherwise axially displace the sleeve 16 relative to the clamp 22 so as to enable the jaws 26 of clamp 22 to move away from one another and, thereby, release the needle cannula 32 for retraction into the empty medication carpule 2.

Having thus set forth a preferred embodiment of the present invention, what is claimed is:

1. A syringe comprising:
   a hollow cylinder having proximal and distal ends;
   a cartridge located within said cylinder and containing a supply of fluid;
   a needle cannula having a first end extending outwardly from the distal end of said cylinder and a second end projecting into said cylinder to communicate with said cartridge so that the fluid supply may be injected from said cartridge via said cannula;
   means to releasably retain said cannula at the distal end of said cylinder, said retaining means including a set of normally spaced jaws that are movable towards one another and into engagement with said cannula;
   means to surround said cannula retaining means and thereby move said jaws thereof towards one another and into engagement with said cannula; and
   means to displace one of said retaining means or said surrounding means relative to the other of said retaining means and said surrounding means so that said jaws are free to move away from one another and out of engagement with said cannula to permit said cannula to be removed from said jaws.

2. The syringe recited in claim 1, further comprising respective positioning means formed on each of said surrounding means and said cannula retaining means, said positioning means being detachably interconnected with one another to oppose the displacement of the one of said retaining means or said surrounding means relative to the other so as to prevent said cannula from being removed from the jaws of said cannula retaining means.

3. The syringe recited in claim 2, wherein said respective positioning means are complementary threads that are rotated into engagement with one another.

4. The syringe recited in claim 2, wherein said respective positioning means are complementary series of alternating ridges and valleys that are snapped into engagement with one another.

5. The syringe recited in claim 1, wherein said surrounding means includes a generally hollow, cylindrical body having first and second ends, the first end of said body receiving at least some of said medication cartridge therewithin, and the second end of said body receiving at least some of said cannula retaining means therewithin.

6. The syringe recited in claim 1, wherein said cannula retaining means has an annular lip extending around one end thereof, said annular lip engaging said surrounding means to limit the displacement of the one of said retaining means or said surrounding means relative to the other.

7. The syringe recited in claim 1, wherein the means to displace the one of said retaining means or said surrounding means is said medication cartridge, said cartridge being movable axially through the cylinder of said syringe and into contact with said retaining means or said surrounding means.

8. The syringe recited in claim 7, further comprising means for moving said cartridge axially through the cylinder of said syringe and into contact with the one of said retaining means or said surrounding means.

9. The syringe recited in claim 8, wherein the means for moving said cartridge axially through said cylinder is a piston assembly having a piston movable axially through said cartridge and a piston stem connected to said piston for moving said piston through said cartridge, such that an axially and distally directed force applied to said piston stem is transferred, via said piston, to said cartridge for advancing said cartridge distally through said cylinder and into contact with one of said cannula retaining means or said surrounding means.

10. The syringe recited in claim 1, further comprising means for retracting said needle cannula into said cartridge at the interior of said syringe cylinder after the fluid supply of said cartridge has been injected and the jaws of said cannula retaining means have been moved away from one another and out of engagement with said cannula.

11. The syringe recited in claim 10, wherein the means for retracting said needle cannula is a piston which is movable distally through said cartridge for expulsing the supply of fluid therefrom and for receiving a portion of said cannula therewithin, said piston also movable proximally through said cartridge to correspondingly retract said cannula completely within said cartridge.

12. The syringe recited in claim 11, wherein said piston has an axially extending nub projecting therefrom to receive and retain said cannula therewithin when said piston is moved distally through said cartridge.

13. For receipt within the hollow cylinder of a hypodermic syringe, a combination needle cannula and cannula lock to be interfaced with a medication cartridge in which a supply of fluid is contained, said combination comprising:

a needle cannula to be received within the cylinder of said syringe so that one end of said cannula is aligned to penetrate said cartridge and communicate with the fluid supply thereof and the opposite end of said cannula extends outwardly from said cylinder to administer an injection;

a needle cannula lock to releasably retain said cannula at the outwardly extending position relative to said syringe cyliner, said cannula lock including a set of spaced jaws that are movable towards one another and into locking engagement with said cannula; and means for moving said cannula lock axially and linearly through said syringe cylinder so that the jaws thereof are free to move away from one another and out of locking engagement with said cannula to permit said cannula to be removed from said jaws.

14. The combination recited in claim 13, further comprising means to surround said cannula lock to thereby move the jaws thereof towards one another and into locking engagement with said cannula, said cannula lock movable axially and linearly relative to said surrounding means so that the jaws of said locking means are free to move away from one another and out of locking engagement with said cannula.

15. The combination recited in claim 14, further comprising positioning means located on each of said cannula lock and said cannula lock surrounding means so as to be detachably connected together to oppose the axial and linear movement of said locking means relative to said surrounding means and thereby prevent the removal of said cannula from the jaws of said cannula lock.

16. The combination recited in claim 15, wherein said positioning means are complementary threads that are rotated into engagement with one another.

17. The combination recited in claim 15, wherein said positioning means are complementary series of ridges and valleys that are snapped into engagement with one another.

18. The cannula recited in claim 14, wherein said cannula lock has an annular lip extending around one end thereof, said annular lip engaging said cannula lock surrounding means to limit the axial and linear movement of said cannula lock relative to said surrounding means.

19. The combination recited in claim 13, wherein the means for moving said cannula lock axially and linearly through said syringe cylinder is the medication cartridge, said cartridge being movable axially through said cylinder and into contact with said cannula lock.

20. The combination recited in claim 13, further comprising means for retracting said needle cannula into said cartridge after the fluid supply of said cartridge has been injected and the jaws of said cannula lock have been moved away from one another and out of locking engagement with said cannula.

21. For a syringe including a hollow cylinder having proximal and distal ends and a fluid filled cartridge received in said cylinder, the combination comprising:

a needle cannula having a first end extending outwardly from the distal end of the cylinder and a second end projecting into the cylinder in alignment with the cartridge;

means for releasably retaining said cannula at the distal end of the cylinder, said retaining means being capable of movement into and out of engagement with said cannula;

means for surrounding said cannula retaining means to thereby cause said retaining means to move into engagement with said cannula; and means for displacing one of said retaining menas or said surrounding means axially and linearly relative to the other of said retaining means or said surrounding means to cause said retaining means to move out of engagement with said cannula and thereby permit said cannula to be removed from said retaining means.

22. The combination recited in claim 21, wherein said cannula retaining means includes a pair of normally spaced jaws that are moved towards one another and into engagement with said cannula when said jaws are surrounded by said surrounding means, said jaws moving away from one another to permit said cannula to be removed therefrom when one of said jaws or said retaining means is displaced axially and linearly relative to the other of said jaws or said retaining means.

23. The combination recited in claim 21, further comprising positioning means disposed at each of said cannula retaining means and said surrounding means and detachably connected to one another to oppose the displacement of the one of said retaining means or said surrounding means relative to the other.

24. The combination recited in claim 21, further comprising locating means disposed at each of said surrounding means and said cartridge and detachably connected to one another to locate the second end of said cannula in spaced, axial alignment with said cartridge.

25. The combination recited in claim 21, wherein said surrounding means is a hollow sleeve that is coaxially aligned with said cannula retaining means and the cannula.

26. The combination recited in claim 25, wherein said sleeve has a first end portion of relatively small diameter at which to receive said cannula retaining means and a second end portion of relatively large diameter at which to receive at least some of said cartridge.

27. The combination recited in claim 26, wherein said cannula retaining means projects inwardly into said sleeve from the first end portion thereof to be arranged in spaced axial alignment with the carpule at the second end portion of said sleeve.

28. The combination recited in claim 27, wherein the cartridge is movable through said sleeve and into contact with said retaining means at the second end portion of said sleeve for displacing said retaining means axially and linearly through the first end portion of said sleeve to cause said retaining means to move out of engagement with the cannula.

* * * * *